(12) United States Patent
Nair

(10) Patent No.: US 6,881,574 B2
(45) Date of Patent: Apr. 19, 2005

(54) NONINVASIVE DETECTION OF COLORECTAL CANCER AND OTHER GASTROINTESTINAL PATHOLOGY

(76) Inventor: Padmanabhan P Nair, 4520 Hemlock Cone Way, Ellicott City, MD (US) 21042

( * ) Notice: Subject to any disclaimer, the term of this patent is extended or adjusted under 35 U.S.C. 154(b) by 155 days.

(21) Appl. No.: 09/755,233

(22) Filed: Jan. 8, 2001

(65) Prior Publication Data

US 2001/0026924 A1 Oct. 4, 2001

Related U.S. Application Data

(62) Division of application No. 09/292,358, filed on Apr. 15, 1999.

(51) Int. Cl.[7] ............................. C12N 5/00; C12N 5/02; C12N 5/06; C12N 5/08

(52) U.S. Cl. ....................... 435/325; 435/378; 435/363; 435/366; 435/371

(58) Field of Search ................................. 435/325, 326, 435/328, 327, 334, 347, 365, 366

(56) References Cited

PUBLICATIONS

Kobayashi et al (J. Immunol., 1989, 143(8)2567–2574).*
Dutta et al (Gastroenterology, 1995, 108(4 SUPPL)A463).*

* cited by examiner

*Primary Examiner*—Susan Ungar
(74) *Attorney, Agent, or Firm*—Mishrilal Jain

(57) ABSTRACT

A method for isolating viable, biologically substantially pure exfoliated fecal colonocytes at normal ambient temperature is described. Immunocoprocytes and inflammatory cells indicative of certain gastrointestinal conditions and a noninvasive method for detecting colorectal cancer are set forth. Composition of transport and suspension media for isolation of colonocytes are detailed.

4 Claims, 3 Drawing Sheets

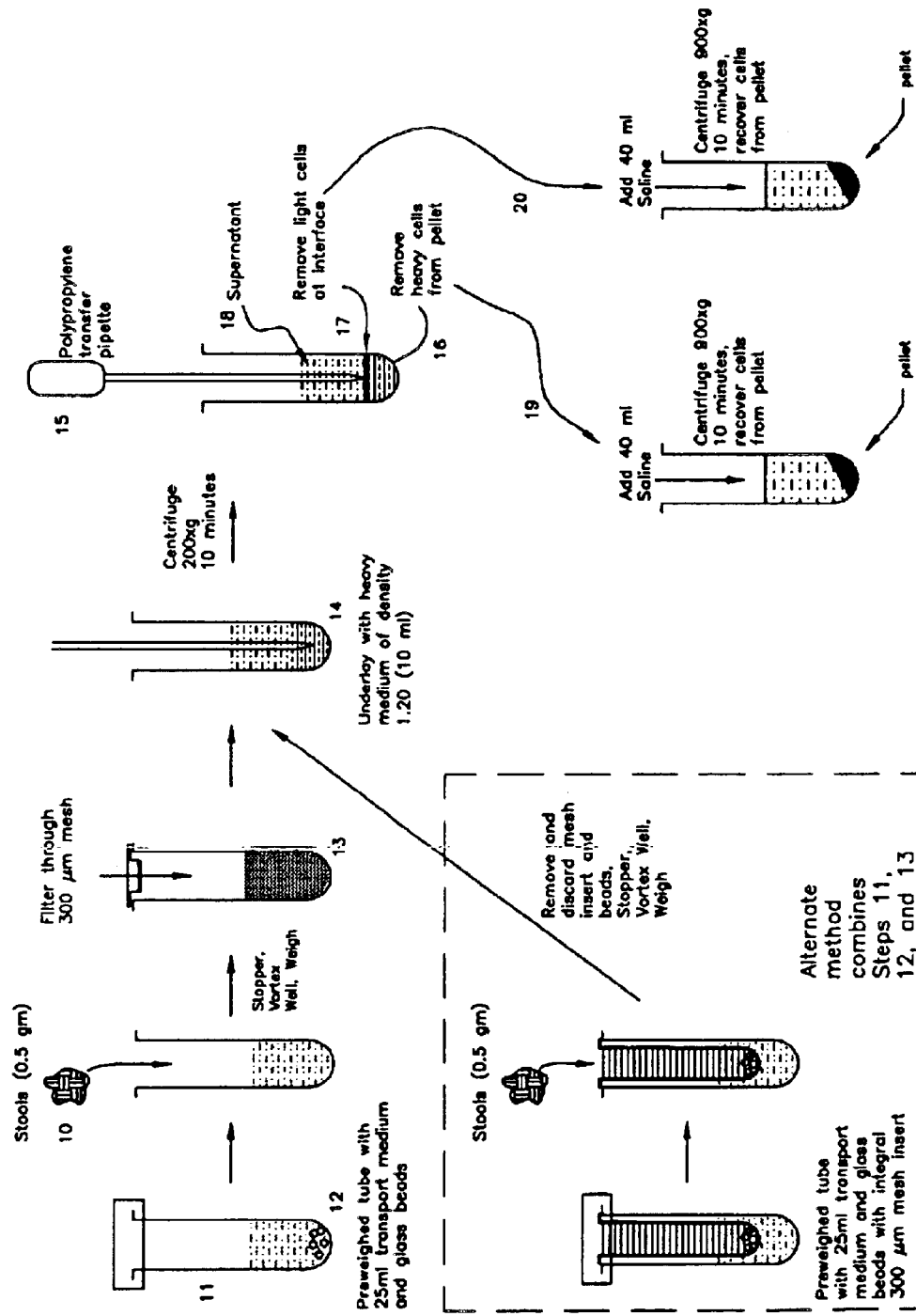
Fig. 1 Schematic representation of the steps in the isolation of viable, substantially pure colonocytes.

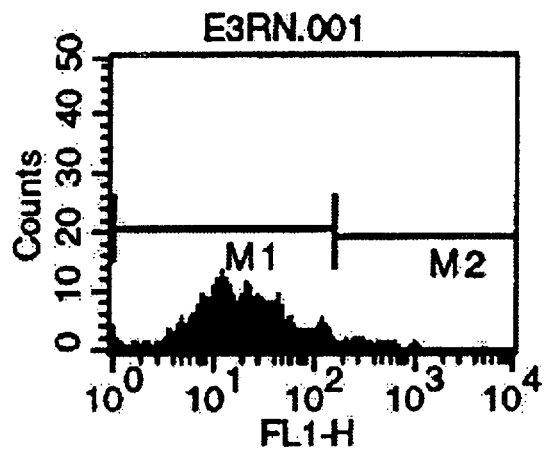

Histogram Statistics

File: E3RN.001
Sample ID: colonic cells
Tube:
Acquisition Date: 8-Dec-98
Gated Events: 1469
X Parameter: FL1-H (Log)

Log Data Units: Linear Values
Patient ID:
Panel:
Gate: G3
Total Events: 10000

| Marker | Left, Right | Events | % Gated | % Total | Mean | Geo Mean | CV | Median | Peak Ch |
|---|---|---|---|---|---|---|---|---|---|
| All | 1, 9910 | 1469 | 100.00 | 14.69 | 36.30 | 20.00 | 179.56 | 18.11 | 11 |
| M1 | 1, 165 | 1418 | 96.53 | 14.18 | 26.09 | 18.15 | 97.70 | 17.00 | 11 |
| M2 | 165, 9910 | 52 | 3.54 | 0.52 | 317.36 | 293.10 | 45.83 | 278.81 | 198 |

Fig. 2 Histogram data from flow cytometry of isolated colonocytes in accordance with the procedure of the present invention showing a purity of 96.5%. The numbers in the abscissa represent the size distribution of the cells. The numbers in the ordinate represent cell counts. M1 represents the single peak detected by the flow cytometer and M2 indicates the residual impurity.

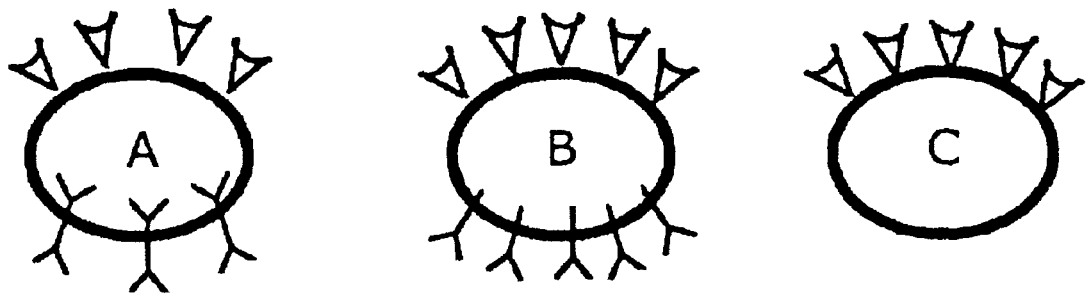
Fig. 3 Diagrammatic representation of classes of immunocoprocytes identified on the basis of their immunoglobulin characteristics. A: Immunocoprocytes coexpressing chimeric IgC and CFc receptors.
B: Immunocoprocytes coexpressing IgA and CFc receptors. C: Immunocoprocytes expressing only CFc receptors.

NONINVASIVE DETECTION OF COLORECTAL CANCER AND OTHER GASTROINTESTINAL PATHOLOGY

This is a divisional of application Ser. No. 09/292,358 filed Apr. 15, 1999.

BACKGROUND OF THE INVENTION

1. Field of the Invention

The present invention is related to isolated colonocytes enabling early noninvasive detection of colorectal cancer and other gastrointestinal diseases. More particularly, the present invention is related to isolated, biologically substantially pure and viable immunocoprocytes and nonepithelial cells of lymphoid origin obtained from a small fecal sample. The invention is further related to providing a transport medium and a dispersion or suspension medium for isolating viable colonocytes from a fecal sample at normal ambient temperature and a method for detecting colorectal and other gastrointestinal pathology employing the isolated colonocytes of the present invention. The isolated colonocytes also allow the study and determination of other anomalous conditions, symptoms, disorders or pathological conditions.

2. Prior Art

A common gastrointestinal malignancy in humans is colorectal cancer. It has been estimated that colorectal cancer accounts for approximately 14% of all cancer-related deaths in men and women in the United States and its incidence continues to be high (Boring et al, CA Cancer J. Clin. 1994; 44:7–26). Early detection is a critical factor in successful treatment of this cancer, as it is in the treatment of other malignancies.

Screening approaches to detection of colon and colorectal tumors are presently based on the use of (a) fecal occult blood test (FOBT), (b) flexible sigmoidoscopy, (c) double contrast barium enema, and (d) colonoscopy. Among these screening tests only FOBT, which is based on a relatively high probability of bleeding from colorectal tumors, is noninvasive, simple and relatively inexpensive. However, frequent false positive and false negative results of the FOBT considerably limit its specificity and sensitivity. Other procedures are expensive and invasive. Hence, there is a clear need for providing a simple, noninvasive, reliable and inexpensive method for detecting colorectal cancer, gastrointestinal (GI) tract diseases and other pathological conditions.

Colonocytes represent an important source of informational marker molecules that provide a picture of the immediate past metabolic history of the GI tract of a subject. In addition, such cells are representative of the cell population from a statistically large sampling frame reflecting the state of the colonic mucosa along the entire length of the colon in a non-invasive manner, in contrast to a limited sampling by colonic biopsy using an invasive procedure involving endoscopy.

Colonocytes undergo certain changes or transformations and carry certain biological or chemical markers indicative of colonic pathologies including precancerous and cancerous conditions. Therefore, the colonocytes could serve as a valuable early indicator of the onset of neoplastic processes and other pathophysiological changes in the GI tract. Subtle changes in the genes and surface proteins are examples of such neoplastic markers. In particular, Ki67, the cell surface glycoprotein CD44 and tumor-associated antigens 19-9 and lectin binding are specific biomarkers of neoplastic transformation in the GI tract. There is also a strong correlation between the amount of DNA in isolated colonic cells and the presence of tumors, because rapidly dividing cells contain more DNA. It is also well recognized that the development of colonic adenomatous polyps and cancer is a multistep process involving activation of oncogenes (ki-ras), inactivation of tumor-suppressor genes (p53 and APC), and alterations in the DNA mismatch repair genes.

Heretofore, it was generally understood in the art to which this invention belongs that exfoliated colonic cells are destroyed once they are shed into the stools, the reason being that these cells start breaking down as soon as they are exposed to the atmosphere. The enzymes, mucus and the bacteria contained in the stool contribute to the process of destroying the colonic cells. Chilling the freshly collected stool sample to the temperature below −20° C. has been described, for example, in U.S. Pat. Nos. 5,094,956, 5,380, 647 and 5,455,160 only for preserving the chemical constituents, without regard to the cellular components. Thus, these procedures do not retain cellular integrity and are not applicable for isolating intact, viable cells free of other impurities.

Dutta and Nair (Gastroenterology, 114:1333–1335, 1998) refer to Albaugh et al (Int. J. Cancer, 52:347–350, 1992) and Iyengar et al (FASEB J. 5: 2856–2859, 1991) for accomplishing isolation of viable colonic cells. Albaugh et al described a transport medium and a procedure to obtain colonocytes from a stool sample based on earlier work of Iyengar et al. However, the transport medium of the prior art was different from the transport medium of the present invention in as much as Albaugh et al's medium consisted of a saline solution to which antibiotics were added in addition to fatty acid free BSA. In other words, the prior art transport medium was deficient at least in one criterion, i.e., in not having a mucolytic agent which is an absolute necessity for the formulation of the transport medium in accordance with the present invention.

Furthermore, in Albaugh et al's system the stool sample after collection had to be kept cooled in ice while being trasported to the laboratory for further processing and could be preserved in ice only for about an hour. In contrast, the system of the present invention does not require cooling in ice and achieves desirable results at the normal ambient temperature which is an important feature of the present invention. Moreover, Albaugh et al state that although their cells had a viability in excess of 80%, the presence of phagocytes and other cells could not be ruled out. Indeed, FIGS. 3 and 4 of Iyengar et al clearly show that the cellular preparations obtained were considerably impure. Thus, the procedures of Iyengar et al and Albaugh et al may provide viable colonocytes, but they are inadequate for the purpose of obtaining substantially pure colonocytes. In summary, heretofore it has not been possible to obtain a viable, biologically subtantially pure sample of a particular cell type isolated at normal ambient atmospheric conditions from a small fecal mass.

SUMMARY OF INVENTION

It is, therefore, an object of the present invention to provide viable, biologically substantially pure exfoliated fecal colonocytes isolated at normal ambient temperature.

It is a further object of the present invention to provide viable, isolated, immunocoprocytes.

It is an additional object of the present invention to provide viable, isolated, inflammatory cells of lymphoid or non-lymphoid lineage.

It is a further object of the present invention to provide a transport medium and a dispersion or suspension medium for isolating viable exfoliated fecal colonocytes at normal ambient temperature.

A further object of the present invention is to provide a noninvasive method for detecting gastrointestinal disorders including colorectal cancer, employing the exfoliated fecal colonocytes isolated at normal ambient temperature in accordance with the teachings of the present invention.

Various other objects and advantages of the present invention will become evident from the detailed description of the invention and from the brief description of the drawings.

BRIEF DESCRIPTION OF THE DRAWINGS

The foregoing and other objects, aspects and advantages will be better understood with reference to the drawings in which:

FIG. 1 is a schematic presentation of the process of isolating viable exfoliated colonocytes at normal ambient temperature from a small sample of fecal material;

FIG. 2 presents histogram data from flow cytometry of isolated colonocytes in accordance with the present invention showing a purity greater than 96%; and FIG. 3 is a diagrammatic representation of classes of colonic cells identified based on their immunoglobulin characteristsics.

DETAILED DESCRIPTION OF THE INVENTION

Various objects and advantages of the present invention are achieved by obtaining viable, homogeneous colonocytes of desired cell types isolated from a fecal sample at normal atmospheric conditions and ambient temperature.

It should be understood that unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the methods and materials described herein are preferred. Unless mentioned otherwise, the techniques employed or contemplated herein are standard methodologies well known to one of ordinary skill in the art. The materials, methods and examples are only exemplary and not limiting.

The term "substantially pure" as used herein means that the product is homogeneous or uniformly of a single type with greater than 96% purity, usually 98%–99% pure, as determined by flow cytometry or by the procedures described herein and is without material interference or contamination of other types of cells.

Heretofore, the problem encountered with exfoliated colonocytes in fecal matter was that these cells got destroyed as soon as exposed to the normal atmospheric conditions due to the presence in the fecal matter of proteolytic enzymes, microflora, mucus and the like. Hence, a system had to be devised to inhibit the action of all those factors or elements which prevented the isolation of intact, living colonocytes at normal ambient temperature from fecal matter. This is achieved by the present invention by formulating two different media: (1) a transport medium, and (2) a dispersion or suspension medium. The transport medium is made of physiological saline solution containing an enzyme inactivating amount of an enzyme trapping or protease sequestering agent, a sufficient amount of a bacteriocidal agent to inhibit bacterial activity, and a mucolytic amount of an agent that destroys mucus contained in fecal matter.

Various enzyme trapping, bacteriostatic and mucolytic agents will be suggested to one of ordinary skill in the art and any suitable agents that do not interfere with the objects of the present invention could be used in the formulation of the transport medium in accordance with the teachings of the present invention.

Preferred among enzyme trapping agents are proteolytic activity inhibitors and animal proteins. Examples of suitable proteolytic activity inhibitors include PMSF, pepstatin A, bestatin and chymostatin. The reagents that inhibit or deactivate enzymatic activity include formaldehyde, metal chelating agents, heavy metal ions, certain amino acids such as tyrosine and phenylalanine, and high concentrations of zinc or inorganic phosphates. Suitable among animal proteins are those that are non-immune, water soluble compounds including serum albumins of rabbit (RSA), goat (GSA), sheep (SHA), horse (ESA), bovine (BSA) and human (HSA) origin. Certain polyamino acids that do not interefere with a later assay procedure could also be used as enzyme deactivating agents. Suitable examples of such polyamino acids are poly-L-lysine, poly-L-proline, poly-l-tyrosine and the like.

Suitable examples of bacteriostatic agents are sodium azide, sodium benzoate, antibiotics (such as penicillin, streptomycin, amphotericin B, gentamicin, polymyxin B and the Like). A preferred bacteriocidal agent is Thimerosal (Sigma Chemical Co.)

Suitable examples of mucolytic agents are guaifenesin, guaiacol, potassium iodide, B-mercaptoethanol, dithiothreitol, capsaicin, glycyrrhizin and the like. A preferred mucolytic agent is N-Acetyl Cysteine (Sigma Chemical Co.).

Puck's Saline G is a preferred source of physiological saline solution.

A preferred transport medium is prepared as follows:

| | |
|---|---|
| Puck's Saline G | 500 ml |
| Sodium Bicarbonate | 350 to 500 mgs |
| BSA | 2.5 to 15 gms |
| N-Acetyl Cysteine | 250 to 500 mgs |
| Thimerosal | 100 to 300 mgs |

The dispersion or suspension medium differs from the transport medium with respect to bacteriocidal agent, e.g., Thimerosal, which is omitted when preparing the dispersion or suspension medium.

Procedure for Isolating Substantially Pure Colonocytes at Normal Ambient Temperature:

Referring now to FIG. 1, a small stool sample 10 (about 1 to 5 gm) is placed into a tube 11 containing a transport medium 12, after which the tube is closed with a stopper. The stool sample 10 is then thoroughly dispersed in medium 12 after which the contents of tube 11 are emptied into a double walled plastic bag 13 (e.g., Stomacher bag with a mesh liner, Tekmar Co.) and diluted with the dispersion medium 14 (about 50 ml/gm of stool, wet weight) and mixed in a mechanical mixer 15 (e.g., Stomacher, Tekmar Co.) for about 30 seconds. The contents of the plastic bag are then allowed to settle down briefly. The aliqot 16 of the plastic bag is then pipetted into 50 ml polypropylene conical centrifuge tubes 17 and underlaid with a heavy medium 18 having a density in the range of about 1.033 to 1.120 (preferably Histopaque 1119, Sigma Chemical Co.) and centrifuged at about 200×g for about 30 minutes in a table top centrifuge with the brakes off.

The colonic cells accumulate as a band at the interface between the heavy medium 18 and the lighter suspension 16 above. This band 19 comprising the desired colonic cells is removed by sucking out with a plastic transfer pipette 20 and placed in a new 50 ml centrifuge tube 21 and diluted with about 40 ml of the dispersion medium 22. The suspension of cells thus obtained is then centrifuged at about 900×g for about 10 minutes after which the clear supernatant is discarded and the cell pellet 23 remaining at the bottom of the centrifuge tube is resuspended in phosphate buffered saline (PBS) 24 containing about 1% bovine serum albumin (BSA). The suspension is then again centrifuged at 900×g after which the clear supernatant is discarded and the pellet 25, comprising substantially biologically pure isolated exfoliated viable colonocytes, is recovered.

For determining the viability of the isolated colonocytes, a portion of the pellet 25 is dispersed in PBS/BSA medium 26 (1 ml/gm of stool sample). Then, a $\frac{1}{10}$ dilution of the suspension is counted in a hemocytometer in the presence of trypan blue. As is well known to a skilled artisan, the cells that do not take up trypan blue are considered to be viable and counted to determine the cell yield.

The tube or vial 11 may be made of any suitable material including plastics, polystyrene, polypropylene and the like.

It is important to note that an inventive aspect of the present invention is the formulation of a transport medium and a dispersion or suspension medium which together allow the exfoliated colonocytes found in the fecal sample to remain viable at the normal ambient temperature during and after the isolation procedure. In other words, the invention enables isolation of intact, living exfoliated colonocytes from a small sample (e.g. 3 gm) of fecal material without chilling or freezing, at normal ambient temperature ranging from about 22° C. to about 24° C. during the entire isolation process. About 8 to 10 million living colonic cells can be obtained from one gram of the stool sample in accordance with the techniques of the present invention.

When maintained at the normal ambient temperature in the suspension medium of the present invention, the isolated colonocytes can be viably preserved for several hours. Table 1 shows cell yields and viability as a function of storage time and temperature conditions.

Of course, alternate techniques could be substituted in the isolation steps. For example, the suspension of the stool sample in the transport medium 12 may be filtered through screens (149 micrometers, 105 micrometers and 52 micrometers). Also, the pellet in the dispersion medium can be gently overlayered on higher density Percoll gradients and centrifuged so that the cells can be recovered from the top of the gradient. Such modifications are common in the art and are included within the purview of this invention.

It is understood, of course, that whenever appropriate a reference or base line would be usually established using colonocytes obtained from disease-free subjects so that a comparative, diagnostic or evaluation study could be made with colonocytes obtained from a subject suspected of a disease or pathological condition.

It was discovered that an important and advantageous feature of the non-invasively obtained colonocytes of the present invention is that these isolated colonic cells carry markers or transformations characteristic of the pathology of the GI tract and, therefore, they can serve as diagnostic and predictor indicators of the GI tract pathology.

Immunocoprocytes

Since the colonic cells isolated from stools were discovered to be true representative of the anatomical and pathophysiological condition of the entire colon, among other utilities these cells also allow monitoring of mucosal immunity. The mucosa of the GI tract is a major site for the elaboration of immunological defenses mediated by immunoglobulins. It was discovered that a functionally distinctive group of cells, designated herein as immunocoprocytes, can be identified and isolated from the exfoliated cells obtained by the methodologies of the present invention. Immunocoprocytes are unique in expressing a specific immunoglobulin designated herein as IgC which is defined as a chimeric immunoglobulin that is recognized by antibodies both to IgG and IgA. Furthermore, immunocoprocytes are clonal, antigen-specific and characterized by the presence of Fc receptors and immunoglobulin A (Ig A).

Given the affinity of immunocoprocytes to IgG and IgA antibodies, several approaches to isolate the immunocoprocytes would be suggested to one of ordinary skill in the art. For example, selective isolation of immunocoprocytes from a mixture of cells obtained from stools, colonic purges or washings, or from surgical and autopsy specimens can be achieved using anti-IgG or a specific anti-IgC monoclonal antibody. The indirect immune adherence approach utilizes a panning technique to allow these cells to adhere to petri dishes coated with anti-IgG or specific anti-IgC antibodies. The use of anti-IgG antibody as a capture agent for immunocoprocytes is based on the discovery in accordance with the present invention that pure IgG expressing monospecific (viz., lacking co-expression of IgA) colonic cells are not detected under normal conditions. Preparation of desired types of monoclonal antibodies are well known to one of ordinary skill in the art and are routinely obtained.

Another approach to obtaining substantially pure immunocoprocytes is the use of fluorescence-activated cell sorting (FACS) technique employing fluorochrome-conjugated anti-IgG or Anti-IgC. In one embodiment, colonic cells are incubated with FITC (fluorescein isothiocyanate) labelled IgG, the excess reagent is washed off and the fluorescently-tagged immunocoprocytes are sorted in a fluorescence-activated cell sorter.

In another embodiment, monoclonal antibodies to IgG or IgC is covalently or non-covalently attached to a solid matrix, such as agarose beads, glass beads, polystyrene beads, hollow fiber, magnetic beads, plastic tissue culture dishes and the like well known to a skilled artisan. Cells that adhere to the antibody coated support are separated from the cell suspension by simply separating the matrix from the suspension by mechanical, magnetic or any other suitable means. As it would be known to one of ordinary skill in the art, the immunocoprocytes can also be bound to the surface of tissue culture flasks coated with anti-IgG or anti-IgC through a linker and after incubating the colonic cell suspension in the flasks, unbound non-immunocoprocytes are decanted off. Bound immunocoprocytes are then recovered by scraping or by appropriate enzymatic cleavage of the linker. Linkers bound to bead matrices (e.g., sepharose) are commercially available (e.g. Pharmacia).

Two-color immunofluorescent flow cytometry is used to determine the number or population of the immunocoprocytes. Colonocytes are incubated with anti-IgG FITC (green fluorescence) and anti-IgA PE (phycoerythrin, red fluorescence). After washing the cells with a buffer to remove the excess antibodies, the cells are then analyzed in a flow cytometer to count the cells with single fluorescence (green or red) and those cells with double fluorescence (both green and red). Cells with double fluorescence are the chimeric Ig C immunocoprocytes, while cells with the red fluorescence are IgA secreting colonic epithelial cells. In most colonic preparations from normal subjects, there is no measurable number of cells recognizing only anti-IgG FITC. In other words, colonocytes bearing only IgG are rare and may be associated with abnormal mucosal or systemic immune dysfunction when they are present.

Analyses of immunofluorescently labelled cells by flow cytometry have revealed the existence of at least three types of colonocytes. To distinguish the Fc receptor of immunocoprocytes from other Fc receptors, the Fc receptor of immunocoprocytes has been designated herein as CFc receptor. Table 2 shows some representative normal distribution of IgC, CFc and IgA found in these cells. A deviation from the normal values would indicate a disease process involving the immune system. FIG. 3 is a diagrammatic representation of at least three types of colonocytes generally detected: "A" shows immunocoprocytes with several unique chimeric immunoglobulin IgC represented by two antibody binding sites on each molecule 2 and several CFc receptors 3. "B" shows colonocytes similar to "A", but with several IgA immunoglobulin molecules 5 along with several CFc receptors 3. "C" shows colonocytes similar to A" and "B", but with no immunoglobulin and only CFc receptors.

Immunocoprocytes, IgA bearing colonocytes and CFC receptor bearing colonocytes described above have distinct roles in immune surveillance of the GI tract and in maintaining systemic humoral immunity of the total organism. These cells perform vital functions: (i) maintaining a balance in the colonization of the colon by microflora; (ii) they are clonal and contain a population of pluripotent cells each one recognizing a single antigen, soluble or particulate, of dietary or biological origin; (iii) they may act as antigen presenting cells to gut-associated lymphoid tissue; (iv) they can be sentinals for detecting invasion by pathogens (e.g., rotavirus, shigella, polio, intestinal parasites, mycobacteria and the like); and (v) their absence can signify a state of immunologic anergy of iatrogenic origin or congenital immunoglobulin deficiencies. Because these colonocytes including the immunocoprocytes, are antigen-specific, they can be immortalized by transformation with carcinogens, oncogene DNA, EBV, SV-40 and the like, to produce antibody-secreting cell lines specific for the selected antigen by hybridoma technology well known to one of ordinary skill in the art.

The following examples illustrate specific utilities of the identified or isolated colonocytes of the present invention. These examples are only illustrative and not limiting in any manner.

EXAMPLE-1

Colonic cells isolated from normal subjects by the procedures described in the present invention are substantially free of any inflammatory cells. In inflammatory bowel disease (IBD), such as ulcerative colitis and Crohn's disease, a significant number of inflammatory cells are mobilized to the surface of the colonic mucosa and are exfoliated along with cells of the epithelium.

One to two gram aliquots of stool collected from IBD patients, suspended in the transport medium are homogenized in a Stomacher with about 150 ml of suspension medium. Aliquots (30 ml) of the suspension are underlaid with 10 ml of Histopaque 1077 (density of 1.077) and centrifuged at room temperature at 200×g for 30 minutes with the brakes off. The interface between the aqueous suspension and the Histopaque 1077 is recovered and washed three times by repeated centrifugation. In this process, inflammatory cells are recovered in addition to the normal complement of colonic cells.

The inflammatory cells in the mixture of cells are tagged with anti-CD45/FITC (green fluorescence) and the positive cells are counted in a flow cytometer. CD45 (cluster of differentiation) also known as leucocyte common antigen, is a lineage-specific marker for lymphoid cells and are present on inflammatory cells. In addition a second marker of inflammation, anti-COX-2/PE (red fluorescence) may also be employed to detect inflammatory cells. Since colonic epithelial cells are negative for CD45, the number of CD45-positive cells in an isolate is a direct measure of the severity of the inflammatory process in IBD. Monitoring of cells positive for both CD45 and COX-2 is an extremely useful non-invasive procedure for following the progression of the disease during the course of treatment.

EXAMPLE-2

Assessment of Status of Mucosal Immunity:

Cells are obtained as described above from subjects who are suspected of having an immunocompromised gut. Aliquots of cells (about 110K) are suspended in PBS buffer and incubated at 37° C. for about 45 minutes with one of the following combinations of fluorescently labelled antibodies: anti-IgG FITC (green), anti-IgA PE (red), and anti-IgC FITC+anti-IgA PE. A parallel tube containing cells with an isotype control antibody is also maintained to account for nonspecific binding antibody. Direct immunofluorescence assays are conducted to measure the binding of antibodies to different sets of colonic cells. A significant decrease in number of immunocoprocytes (expressing IgC) or IgA bearing cells is of diagnostic significance for immune deficiency. Table 2 lists values obtained for normal subjects. Any deviation from the normal values would be indicative of immune dysfunction. It should be noted that direct and indirect immunofluorescence assays can be similarly carried out for the assessment of a repertoire of macromolecules, such as cytokines, signal transduction intermediates, growth factors and the like.

EXAMPLE-3

Expression of Colon Cancer-Associated Biomarkers:

Cells are obtained as described above from patients suspected of having colon cancer or precursors of colon cancer (polyps). In one embodiment of this technique, cells are subjected to indirect immunofluorescence assay for the expression of CD44 or its molecular variants, e.g., CD44V3, CD44V6 and CD44V10; the presence of CD44 or its molecular variants being diagnostic of colon cancer.

EXAMPLE-4

As a source of somatic cells obtainable non-invasively, the colonocytes of the present invention are representative of the phenotype as well as genotype. Thus, they are useful in DNA typing and examination of biological macromolecules (such as DNA, RNA, protein and the like) for determining responses, for example, to pharmacologic and environmental agents and assessment of multi-drug resistance. These isolated cells are also useful in various other ways easily suggested to a skilled artisan.

It should be apparent that given the guidance, illustrations and examples provided herein, various alternate embodiments, modifications or manipulations of the present invention would be suggested to a skilled artisan and these are included within the spirit and purview of this application and scope of the appended claims.

TABLE 1

Effect of storage on cell yields and viability

| Storage Time (Hrs) | Conditions | Cell Yield % | Viability % |
|---|---|---|---|
| 1–6 | Ambient | 100 | 85+ |
| 10 | Ambient | 100 | 65 |
| 24 | 4° C. | 40 | 50 |
| 36 | 4° C. | 24 | 5–6 |

TABLE 2

Distribution of IgC, IgA and CFc bearing colonic cells

| Subject Code | IgC | CFc Receptor | IgA |
|---|---|---|---|
| 308-S1 | 18.5 | 90.3 | 46.5 |
| 308-S2 | 20.8 | 87.8 | 42.0 |
| 318-S1 | 12.2 | 86.9 | 47.7 |
| 318-S2 | 26.5 | 91.2 | 37.7 |
| 319-S1 | 27.5 | 88.9 | 44.0 |
| 319-S2 | 32.9 | 90.9 | 30.0 |
| 325-S1 | 20.2 | 88.9 | 40.0 |
| 325-S2 | 16.8 | 82.2 | 24.0 |

Note:
The numbers represent the % of total cells that carry the corresponding molecule. These results were obtained by flow cytometric analysis of immunofluorescently labelled colonic cells isolated by the technology described in this application.

I claim:

1. Immunocoprocytes isolated from exfoliated colonocytes obtained from fecal matter with a yield of about 8–10 million viable colonocytes per gram of fecal matter, wherein said immunocoprocytes express IgA, IgC, CFc or a combination thereof, wherein said immunocoprocytes expressing IgC are isolated with antibodies to IgA and IgG, wherein said immunocoprocytes expressing IgA are isolated with antibodies to IgA and wherein said immunocoprocytes expressing CFc are isolated with antibody to Fc receptor.

2. The immunocoprocytes of claim 1 expressing IgA and CFc.

3. The immunocoprocytes of claim 1 expressing CFc.

4. The immunocoprocytes of claim 1 expressing immunoglobulin IgC.

* * * * *